United States Patent
Schneider, II et al.

[11] Patent Number: 6,033,222
[45] Date of Patent: Mar. 7, 2000

[54] METHOD OF FABRICATION OF TRANSLUCENT DENTAL RESTORATIONS WITHOUT OPACIOUS SUBSTRUCTURES

[76] Inventors: George J. Schneider, II, 5030 Minton Rd. NW. Suite B, Palm Bay, Fla. 32907; Lawrence Taub, 277 New York Ave., Jersey City, N.J. 07307

[21] Appl. No.: 09/064,766

[22] Filed: Apr. 23, 1998

Related U.S. Application Data

[60] Provisional application No. 60/044,269, Apr. 25, 1997.

[51] Int. Cl.⁷ .................................................. A61C 13/08
[52] U.S. Cl. ........................ 433/203.1; 433/223; 264/20
[58] Field of Search ................................. 433/203.1, 26, 433/212.1, 218, 223; 264/19, 20

[56] References Cited

U.S. PATENT DOCUMENTS

| | | | |
|---|---|---|---|
| 4,650,418 | 3/1987 | Blair et al. | 433/203.1 |
| 4,778,386 | 10/1988 | Spiry | 433/45 |
| 5,127,835 | 7/1992 | Yamaguchi et al. | 433/218 |
| 5,308,243 | 5/1994 | Emmons | 433/203.1 |

*Primary Examiner*—John J. Wilson
*Attorney, Agent, or Firm*—M. K. Silverman

[57] ABSTRACT

A series of die spacers of differing shades are used to match or replicate an assortment of tooth stump or dentin tooth shades. Such die spacers correspond to shades of various manufacturers. This allows the dentist to approximate the proper shade of the tooth preparation in his prescription of a translucent restoration which is communicated to the technician. The technician then applies onto the die of the tooth preparation a die spacer closely matching the chosen tooth stump shade, allowing the technician to wax-up over the die with the selected die spacer. The die spacer retains the traditional function of creating the necessary space under the wax pattern or wax-up. After removal of the wax-up from the die, it is processed, following the manufacturer's procedures, to make a non-opacious substructure of, for example, a translucent ceramic restoration. The dental lab technician readily is then able to return to the patient's original tooth color preparation to complete the fabrication of the translucent restoration (bridge, crown, onlay, inlay or veneer) in accordance with the dentist's prescription.

6 Claims, 14 Drawing Sheets

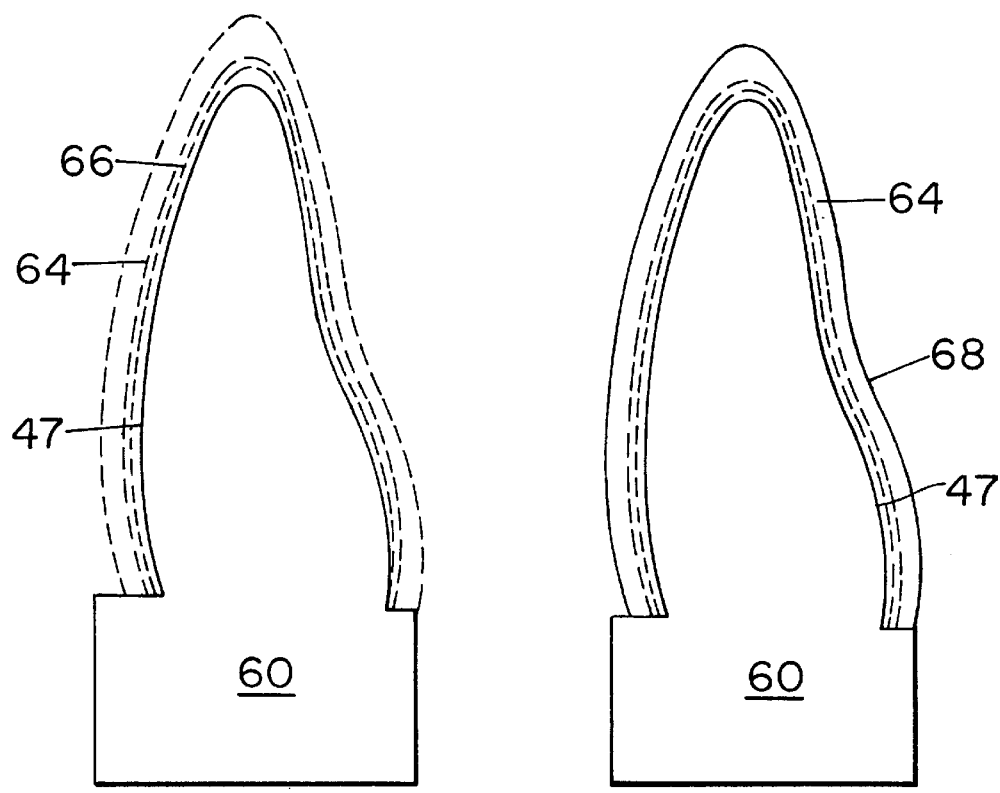
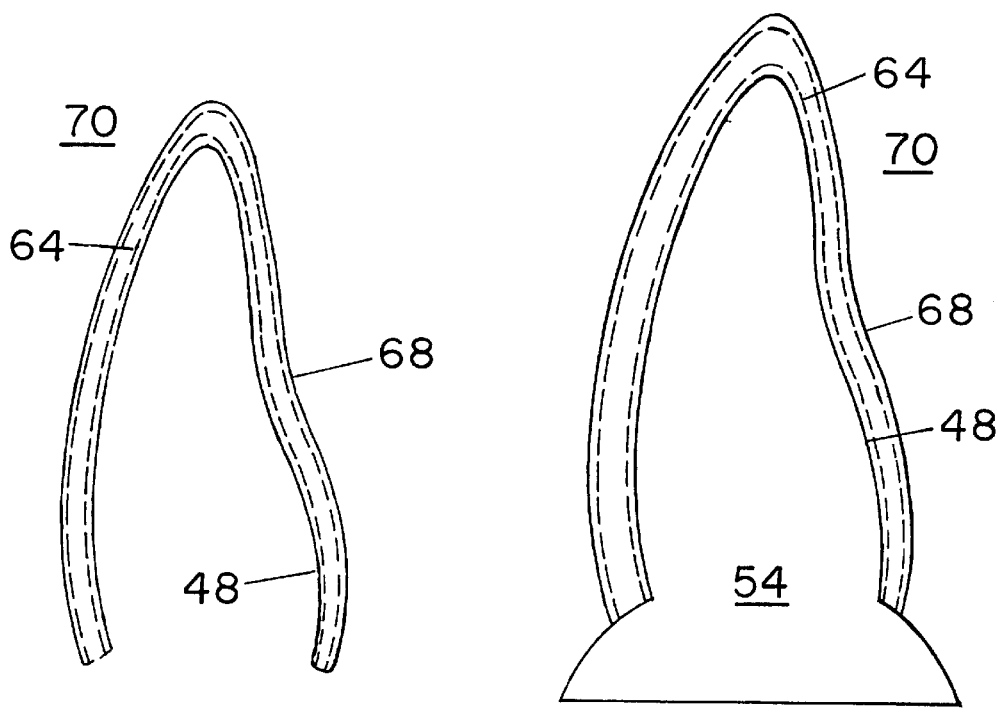
FIG. 17   FIG. 18   FIG. 19   FIG. 20

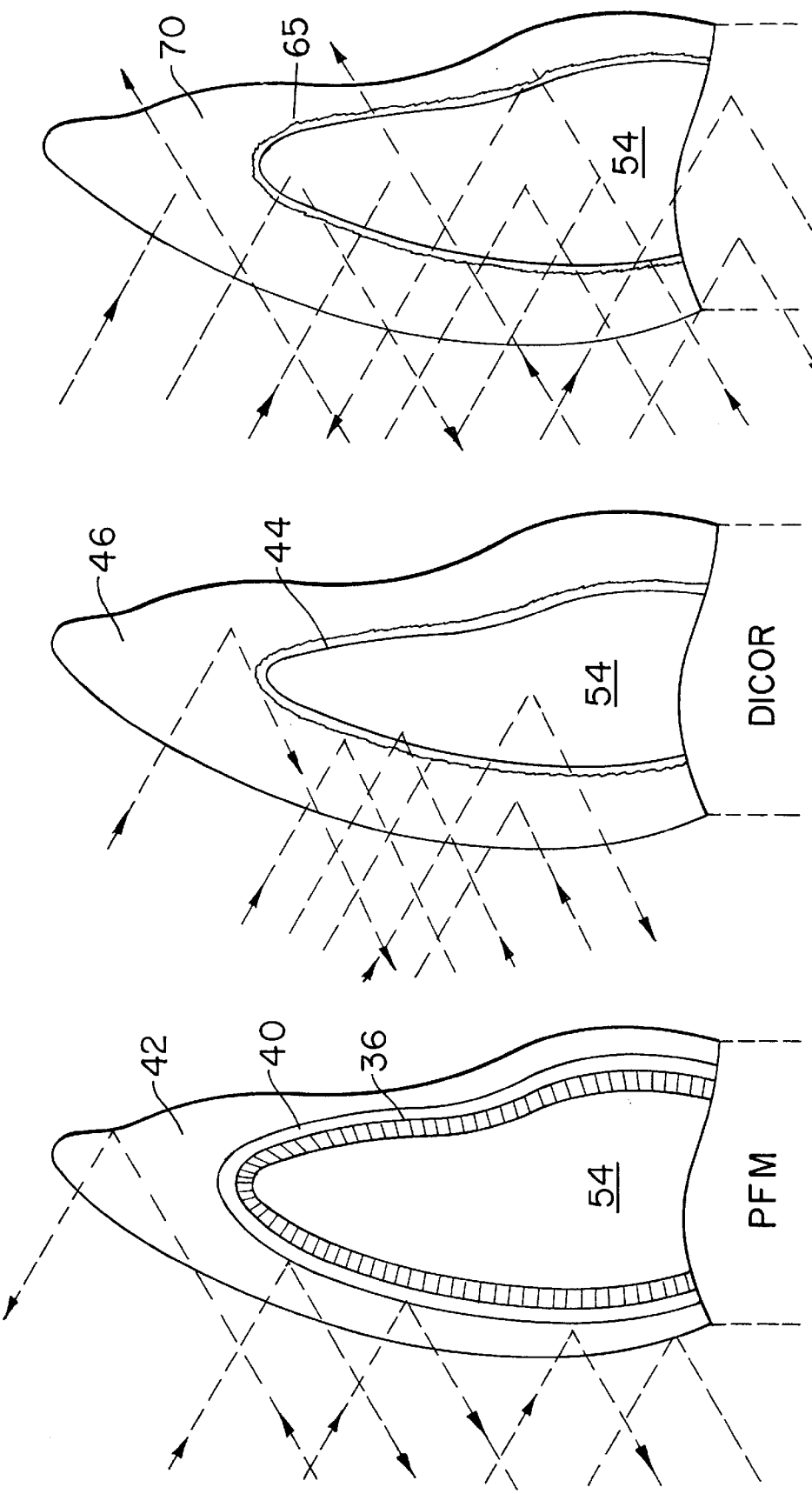

METHOD OF FABRICATION OF TRANSLUCENT DENTAL RESTORATIONS WITHOUT OPACIOUS SUBSTRUCTURES

REFERENCE TO RELATED APPLICATION

This application corresponds in subject matter to that of Provisional Application for Pat. No. 60/044,269, filed Apr. 25, 1997.

BACKGROUND OF THE INVENTION

The prior art of metal substrate dental technology and metal ceramic technology, the latter of which has been a standard in clinical dentistry for more than thirty years, has entailed a number of exacting steps to create the ultimate restoration. These steps are generally as follows:

1) Tooth preparation. Removal of 1.5 to 2 mm. of tooth structure, i.e., enamel or dentin to provide a preparation of the tooth without undercuts and to allow a final metal ceramic or metal resin restoration that is of adequate thickness.

2) Impression (negative mold): Use of an impression material such as a hydrocolloid, polyester rubber, or vinyl polysilicone (VPS) to make impression of tooth preparation.

3) The impression is then used by the laboratory technician to create a stone or epoxy model with removable dies that are an accurate copy of the prepared tooth, i.e., to create a positive replication of the tooth.

4) Painting of a die spacer onto the die, which affords appropriate relief in a range of 20 to 36 microns to allow space for a dental cement or bonding agent to secure the final restoration to the patient's prepared tooth.

5) A lubricant or a release agent is then placed over the die spacer.

6) A wax pattern is then fabricated over the lubricated die.

7) The wax pattern is then invested in high heat investment material and cast from a molten metal using the "lost wax" technique and a centrifuge process to form a metal coping or substructure of the restoration.

8) The ceramic or visible portion of the restoration is then formed by applying and baking successive layers of porcelain powders mixed with distilled water or other types of porcelain building-up liquids, first to opaque over the metal coping to hide the metal color and then to shape the porcelain from its various transition shades to create as natural an appearance as possible. The temperatures of this baking is a function of individual vendor's particular protocol.

Recent technologies now provide systems in which a metal substrate or substructure is no longer required. Therein, the restoration is fabricated using pressable ceramic that can be made and processed by use of lost wax technology to create ceramic substructures. Such ceramic substructures formed therefore require the fabrication of a second shading die. This die is fabricated from a light cured resin stump of the pressable ceramics. It is fabricated by packing this stump material into the ceramic substrate which first coated with a liquid separator, and inserting a plastic holding rod into the resin stump material. The technician cures the material by holding it under a curing light for approximately 1–2 minutes per die. After curing, the remain stump die is removed, a wetting agent is placed over the die, and the die is then put back into the ceramic substrate allowing the technician to do the coloration. The wetting agent permits the transmission of color of the stump material through the substrate. This process includes costly materials and is most time consuming for the technician as compared to the instant invention.

In the invention, for the technician to correctly complete the extrinsic color shading technique on the original die, a die spacer color, matched to the intrinsic stump guide, is needed. This die spacer is opaque and masks out any shade of the die stone used to fabricate the die replacing it with the correct dentin or intrinsic shade. Due to such use of the die spacer, the dental ceramic substructure will have the proper relief for the bonding resin when the restoration is placed on the tooth preparation of the patient. This die spacer is used both to wax up over to create the spacer for the cement as well as for finalizing the extrinsic shades. Thereby only one die preparation is needed.

One of the most exacting and time consuming aspects in the making of a pressed porcelain restoration is that of properly matching the color of the restoration to that of the natural tooth of the patient. Color, in the context of clinical dentistry, has evolved as a complex combination of art and science in which color is differentiated into discreet concepts of hue, value, and chroma. Therein, hue is defined as the dimension of color that enables one to distinguish one family of color from another. Value is defined as the parameter of color that permits one to describe the relative whiteness or blackness thereof, while chroma, as the third dimension of color, defines the relative concentration, strength, saturation or intensity of hue. That is, the more intense a color is, the higher is its chroma level.

These qualities follow the Munsell color system for designating color which employs three perceptually uniform scales (Munsell hue, Munsell value and Munsell chromo) defined in terms of daylight reflection. (McGraw-Hill Dictionary of Scientific and Technical Terms—3rd Ed.). Translucency or the quality of transmitting and diffusing light, provides a perception of depth that is also an important parameter.

The art of coloration of new ceramic/porcelain restorations has been substantially the same as that of traditional metal-ceramic technology. That is, such prior art has related to a variety of techniques of surface treatment including techniques of staining, glazing, and polishing to attempt to correct the hue, chroma, or value of a restoration to that of the natural tooth of the patient. In this process, the starting point has always been that of opaquing the bottom surface of the restoration. However, in the new, all-porcelain and/or pressable ceramic techniques (as applicable to the crowns, onlays, inlays, veneers and bridges), the color of the above-referenced die spacer is of enhanced importance because, unlike metal-to-ceramic technology, there does not exist a metallic or opaque substructure to the pressable ceramic restoration. Accordingly, the effect of the die spacer on the color of a pressable ceramic restoration is most influential in the process of coloration of the pressable ceramic cast restoration.

In the prior art, the role of the die spacer has never been that of matching, or attempting to match, the hue, value or chroma of a tooth preparation or dentin shade, this as noted above, because the dental metal substructure of traditional metal-to-ceramic technology created an opaque inner coping to the restoration. Therefore, the die spacer was never visible. Die spacers have been designated to match the shading of opaque cement. But these opaque cements prevented the need to have die spacers to match the dentin shades. For example, U.S. Pat. No. 4,650,418 (1987) to Blair, held by Dentsply, which teaches the DICOR method, employs internal coloration of a dental cement to modify or correct external of duplicating the shading of the opaque cement which was color coordinated to the extrinsic shade of the shade guide.

Dental die spacers used in the present system (the instant invention) do not attempt to match a dental cement, but rather match the shading of the dentin of the patient's tooth stump, while using a clear resin cement. Therefore, the instant system uses an entirely different basis of coloration.

The instant invention addresses the new requirements and opportunities of color science in clinical dentistry associated with the all porcelain and pressable ceramic (or other clear material) restorations resultant from the fact that such new systems do not utilize a substrate which is inherently opaque.

SUMMARY OF THE INVENTION

In the instant invention, a series of die spacers of differing shades are used to match or replicate an assortment of tooth stump or dentin tooth shades. Such die spacers correspond to shades of various manufacturers. This allows the dentist to approximate the proper shade of the tooth preparation in his prescription of a translucent restoration which is communicated to the technician. The technician then applies onto the die of the tooth preparation a die spacer closely matching the chosen tooth stump shade, allowing the technician to wax-up over the die with the selected die spacer. Therein the die spacer retains the traditional function of creating the necessary space under the wax pattern or wax-up as it is also termed. After removal of the wax-up from the die, it is processed, following the manufacturer's procedures, to make a non-opacious substructure of, for example, a translucent ceramic restoration. Therein, the dental lab technician readily is able to return to the patient's original tooth color preparation to complete the fabrication of the translucent restoration (bridge, crown, onlay, inlay or veneer) in accordance with the dentist's prescription. Die spacer as; used above may include, without limitation, use of stain color modifiers, clear latex spacers, vinyls, teflons and PE materials.

It is thereby an object of the present invention to provide a new die spacer system having shades that enable matching of the dentin or tooth stump to permit the dental technician to more exactly judge the color of the final non-metallic restoration.

It is another to provide dental restorations with superior esthetics and appearance.

It is a further object of the invention to provide an easier method of producing superior esthetics in dental restorations.

It is a still further object to provide a method of producing dental restorations that enable more efficient and less expensive correction of mistakenly produced hues, chromas and values.

It is another object to permit the technician to provide an internal dentin shade on the original preparation die (formed from an impression material) upon which the restoration is to be fabricated.

It is a yet further object of the invention to provide an internal tooth colored die spacer which enhances the quality of shading on all pressable ceramics and other materials by permitting the technician to properly view the color from within to correctly modify the external shading of the porcelain or composite resin while it is on the original (and only) die preparation.

It is a still further object to use an original die preparation as the only necessary die preparation so that the resultant cast non-metallic translucent restoration will exactly match the surface upon which was fabricated to thereby prevent possibly breakage of an otherwise fragile restoration that might otherwise be placed on non-protective surfaces.

It is a further object to eliminate the need which exists in the prior art to fabricate a second die made of a stump-like material onto which the final restoration is placed for purposes of color matching in accordance with the patient's original stump tooth shade.

It is yet further object of the invention to allow the technician to better determine, through the above-referenced insertion of the cast restoration onto the original preparation, if any dimensional distortion has occurred during the firing of the cast restoration by placing the same back into its original preparation.

It is a further object of the invention to allow the technician to use a solid contact model for multiple unit cases, to be able to paint the color corrected die spacer onto each of the preparations of the solid model and to allow all units to be evenly colored after finalization of the interproximal contact.

The above and yet other objects and advantages of the invention will become apparent from the hereinafter set forth Brief Description of the Drawings and Detailed Description of the Invention, set forth herein.

BRIEF DESCRIPTION OF THE DRAWINGS

FIG. 17 shows the re-positioning of the substructure of FIG. 16 to the dental die of FIG. 12, and placement of a wetting agent over the die spacer before repositioning of the ceramic substructure.

FIG. 18 shows the extrinsic coloration over substructure. Intrinsic shade of die spacer is visible through translucent substructure allowing technician to apply appropriate extrinsic shading material to match prescribed tooth shade.

FIG. 19 shows the restoration removed from the dental die of FIGS. 17 and 18 and the application of a translucent bonding resin to the inner surface of the restoration.

FIG. 20 shows the application of the ceramic restoration to the tooth stump of the tooth to be restored.

FIGS. 21 through 23 are conceptual views showing patterns of light reflection and refraction in the various prior art methods, that is, PFM in the case of FIG. 21, and DICOR in the case of FIG. 22, this relative to the patterns of light reflection and refraction in the present inventive method shown in FIG. 23.

DETAILED DESCRIPTION OF THE INVENTION

At present, die spacers are manufactured, typically of brightly colored materials similar to nail polish, model dope, latex liquid, glues such as cyanoacrylate, epoxy solutions, and an assortment of other resins and gels, which are water, solvent or monomer based. Also, there exist polymeric die spacers that operate upon principles of polymerization, light curing, and air or heat drying. These products are designed to provide a specific film thickness, such as six, twelve, fifteen, twenty four, thirty or more microns, of space to the die or preparation surface, often requiring more than one application. The traditional function of the die spacer, as above described, has been that of assuring that the ultimate restoration, when formed, will include sufficient relief (dimension) to enable application of a suitable quantity of bonding material cement without upsetting the desired position or orientation of the restoration within the clinical environment. Colors of traditional die spaces include varying shades of primary and secondary colors, such as red, blue, yellow, orange, grey, green, brown, silver and gold, and have been applied through a variety of means including brush, felt tip pen, dipping, spraying, curing by solvent or water evaporation, and polymerization by chemical or light activation.

Figure 1:
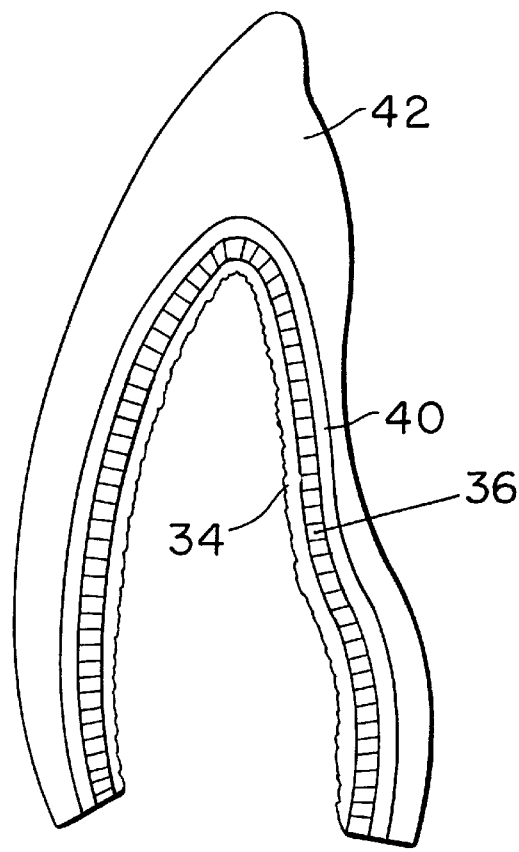
FIG. 1 is a cross-sectional view showing a prior art porcelain fused to metal (PFM) dental preparation.
Figure 2:
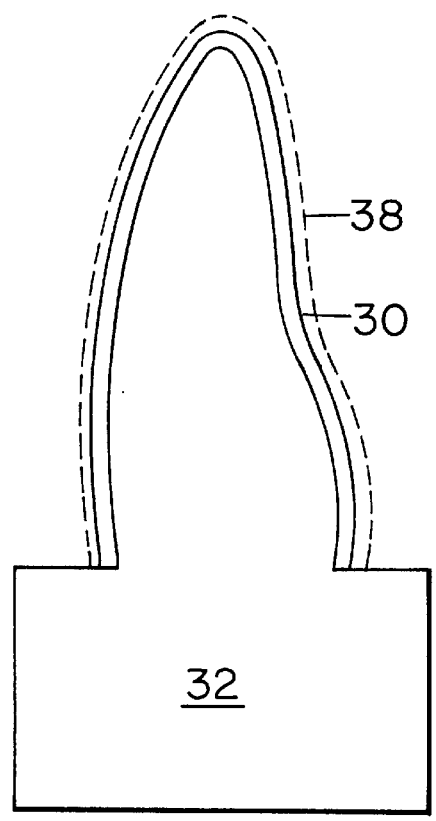
FIG. 2 is a cross-sectional view of a prior art to die used in the formation of the preparation of FIG. 1.

Die spacers have also been designed for the adding or building-up of a uniform space within a die preparation made by a dental technician, dentist or computer controlled machine to allow for sufficient extra space (typically 25 microns) under the restoration fabricated in the wax or other material (burned-out during the investing process) to thereby afford proper space for cement or other bonding material within the restoration. This traditional use, as it exists in porcelain fused to metal (PFM) technology is shown in FIGS. 1 and 2. A die spacer 30 thereby creates a controlled relief on the die 32 prior to wax-up of the cast restoration to thereby provide room for cement bonding 34 under a metal coping 36. Over the die spacer 30 is applied a lubricant or release agent 38. It is also noted that an opaque layer 40 exists between coping 36 and dental build-up material 42. Die spacers, in their historical role, thereby provided better marginal fit, this allowing castings to seat more completely and with less occlusal adjustment. Die spacers also historically acted as high spot indicators by becoming scratched on their surface from contact to a high spot on the internal or underside of the cast preparation as it was being fitted back onto the restoration on which it was formed.

Figure 3:
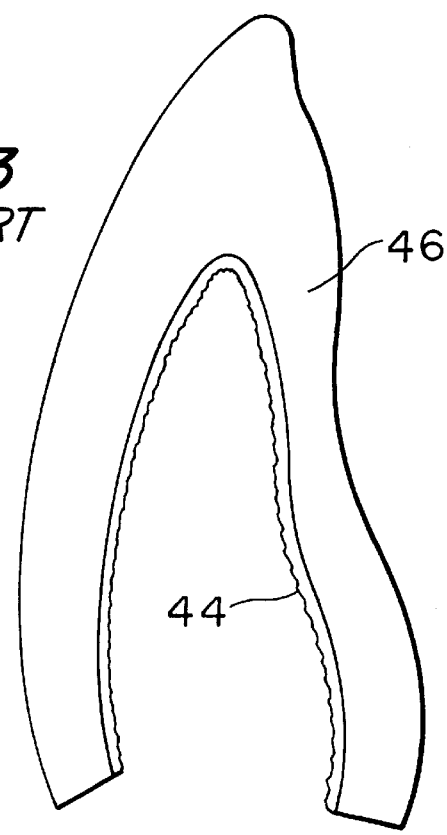
FIG. 3 is a cross-sectional view of a prior art dental preparation using the DICOR castable ceramic method.
Figure 4:
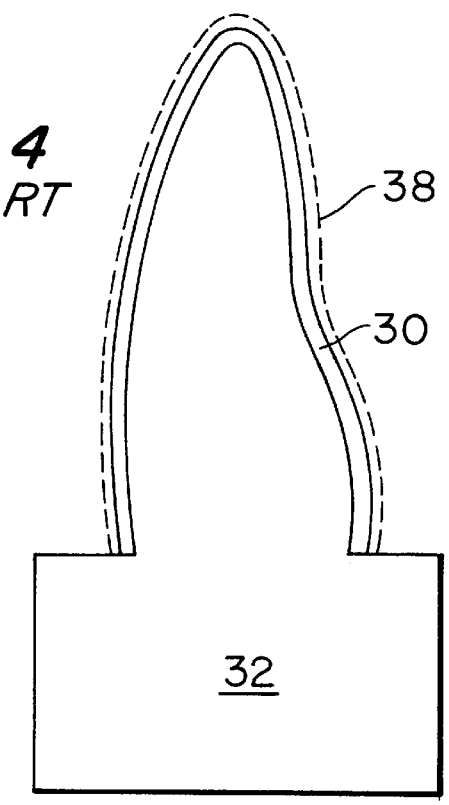
FIG. 4 is a cross-sectional view of a tooth die used in the preparation of FIG. 3.

Such historic die spacers are also used today in a like function in wax patterns or wax-ups used in the fabrication of ceramic, pressable ceramic, or other clear flowable type materials including leucite reinforced ceramics and light curable types of resinous/ceramic polymer materials that have been developed to replace the metal substrate historically, used in metal-to-ceramic technology. See FIGS. 3 and 4, Accordingly, as noted in the Background of the Invention above, the DICOR ceramic technology also requires use of an opaque cement 44. Over cement 44 layers of castable or flowable ceramics 46 are applied to build up the tooth structure. It is noted that the die assembly of FIG. 4 is the same as that of FIG. 2.

As noted in the Background of the Invention, the so-called DICOR method uses the opaque cement 44 as a means of color correction of the ceramic 46. However, in the fabrication of traditional porcelain-to-metal restorations, the color of the die spacer had no bearing on establishing the color of the porcelain. That is, the dental metal substructure, onto which opaque powders, translucent and colored pigments were added and subsequently fused, prevented the color of the die spacer from showing through and therefore played no role in the coloration process of the porcelain of the restoration. In fact, porcelain, given its translucency, required, in the prior art, the opaquing out of the color of the metal substrate to prevent the color of the metal from showing through to the surface of the porcelain. See FIG. 1.

Figure 5:
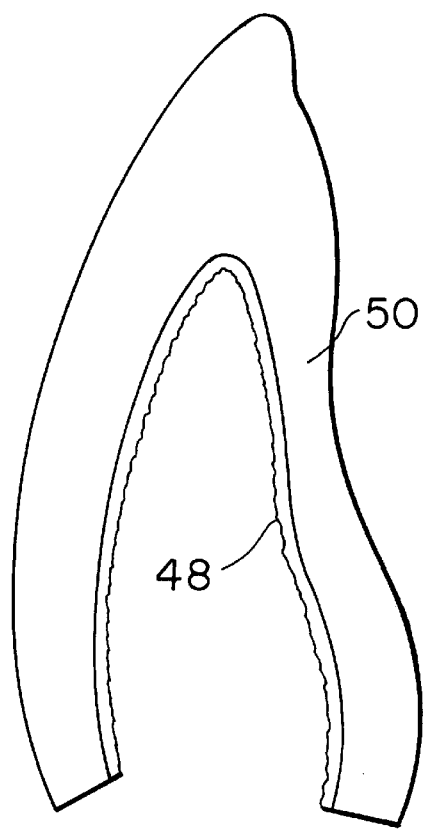
FIG. 5 is a cross-sectional schematic view showing a resultant dental preparation using the present method of fabrication of translucent dental restoration with a non-opacious substructure.
Figure 6:
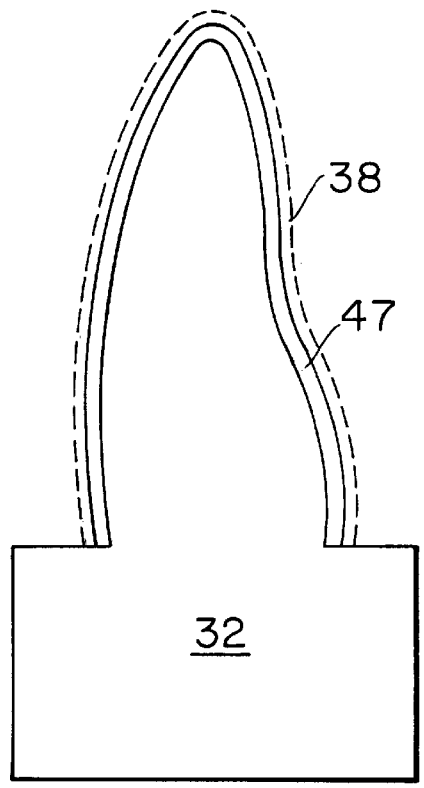
FIG. 6 is a cross-sectional conceptual view of a dental die (more fully described below) used in forming the tooth preparation of FIG. 5.

In the fabrication of newer products, such as IPS Empress (Ivoclar), Optec, (Jeneric Pentron), Inceram-Spinell (Vident) and pressable ceramic restorations, the color of the die spacer assumed, greater significance and, therefore, a mistake in the selection thereof could be detrimental in the overall coloration of the cast ceramic restoration. In the instant inventive method, a die is taken only one time. See FIGS. 5 and 6. Therein is shown the end product of the instant method which is discussed in detail below. However, as may be noted, the new technology of the present invention utilizes a similar die assembly to that of the prior art, namely, the combination of a tooth die 32, a die spacer 30 and a lubricant or release agent 38 (see FIG. 6). However, unlike the prior art, a translucent cement or bonding resin 48 is utilized upon which a tooth build-up of a translucent dental material 50 occurs. As is more fully described below, die spacer 30, as opposed to opaque cement 44 (see FIG. 3) in the DICOR method, functions as the basis of color correction of the translucent material 50. As will be seen below, in the instant method it is only necessary to make only one die of the patient's tooth stump or preparation.

Figure 7:
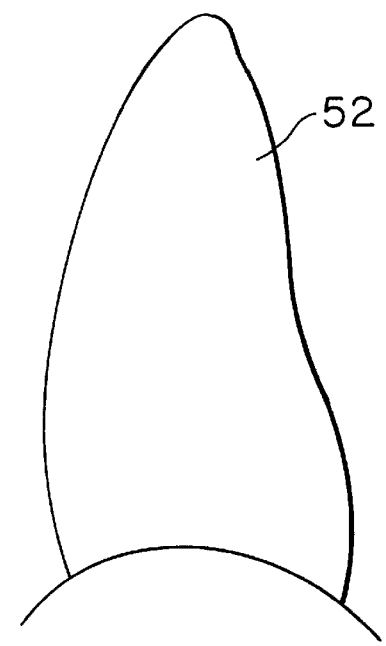
FIG. 7 is a cross-sectional schematic view of a tooth to be restored utilizing the present method of dental restoration.

The present inventive method is more particularly shown with reference to the views of FIGS. 7 through 20 which follow. Therein (see FIG. 7) the process begins by observations by the dentist of the so-called extrinsic coloration, this in terms of the above-defined hue, value, and chroma, of a tooth 52 to be restored. That is, before any reduction of the tooth occurs, the dentist will note the extrinsic hue, value and chroma of the desired restoration.

Figure 8:
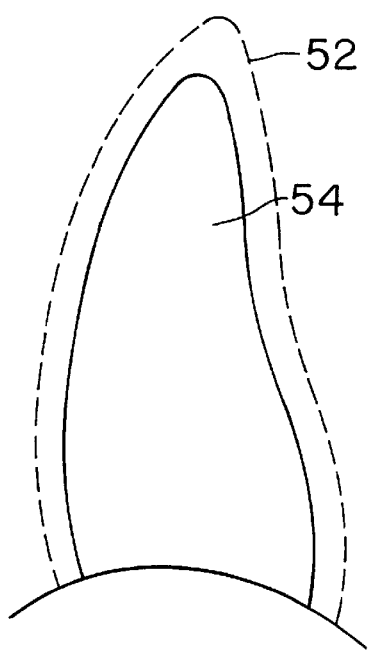
FIG. 8 is a schematic view showing the reduction of the subject tooth.

In FIG. 8 is shown the reduction or cut down of the original tooth 52 to thereby produce the tooth stump or preparation 54 upon which the restoration is to be based. At this time, the dentist will, if deemed necessary by him, generate a prescription of the intrinsic shade or color of the tooth preparation 54. The intrinsic shade or color of the tooth preparation is also known as the dentin color; that is, most of what remains of tooth 52 after the reduction process is the tooth dentin.

Figure 9:
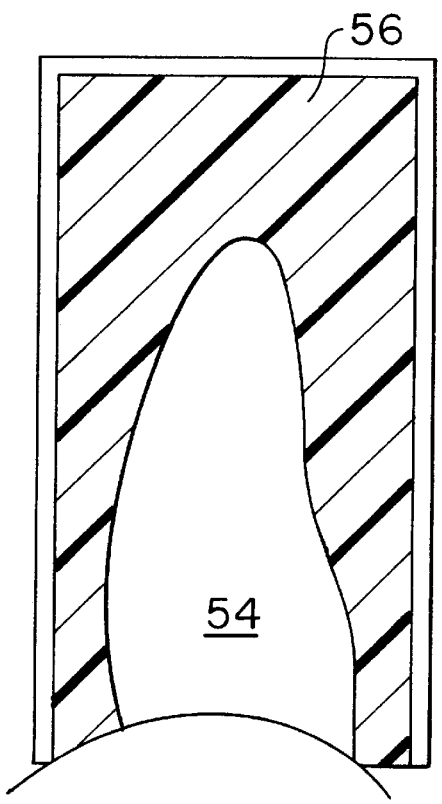
FIG. 9 is a cross-sectional schematic view showing the making of a dental impression about the tooth preparation.
Figure 10:
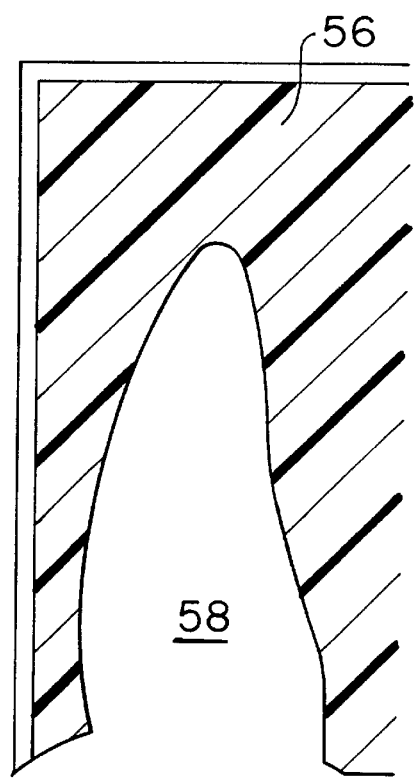
FIG. 10 is a cross-sectional schematic view showing the resultant dental impression after the step of FIG. 9.

In FIG. 9 is shown the application of impression material 56 to the tooth preparation 54. Removal of the impression material from the tooth preparation is shown in FIG. 10. Therein is shown the tooth stump geometry 58. Accordingly, the impression of FIG. 10 will be sent by the dentist to a dental laboratory for use in accordance with the present method.

Figure 11:
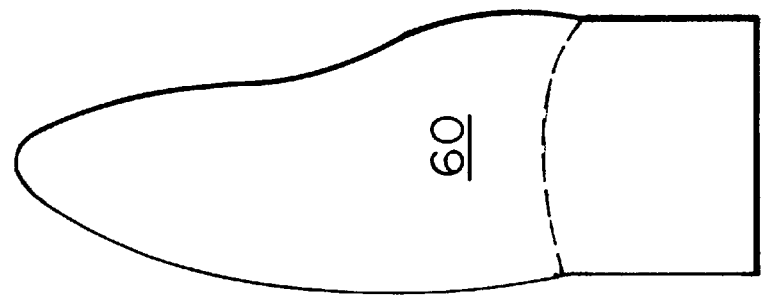
FIG. 11 is a view of the laboratory die resultant from the step of FIG. 10 above.

In FIG. 11 is shown die 60 which is formed at the laboratory by pouring die material into the impression 56. After hardening, the die will comprise an exact replication of the tooth preparation 54. The die 60 therefore constitutes the geometric basis of the dental restoration to be formed.

Figure 12:
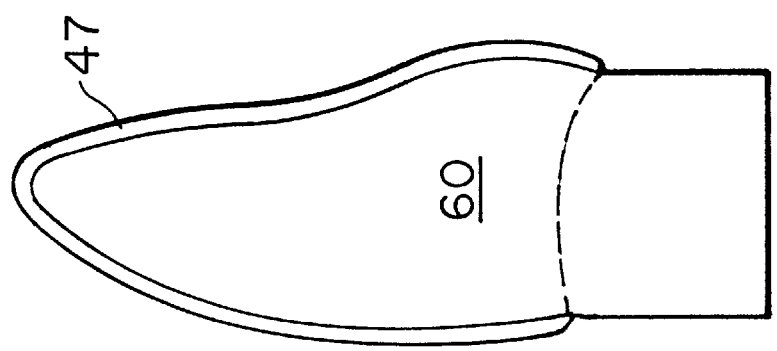
FIG. 12 shows the application of a die spacer, selected in accordance with the invention, to the laboratory die.

In FIG. 12 is shown the application, upon said die 60, of said die spacer 47 to match the dentist's above-referenced prescription of intrinsic tooth color. If there exists a material difference between the patient's stump coloration and the stump guide or intrinsic coloration, as above defined, the dentist may prescribe a die spacer color representing a compromise between these two coloration to further refine the color of die spacer 47 a so-called color modifier, such as a stain, may be used.

Figure 13:
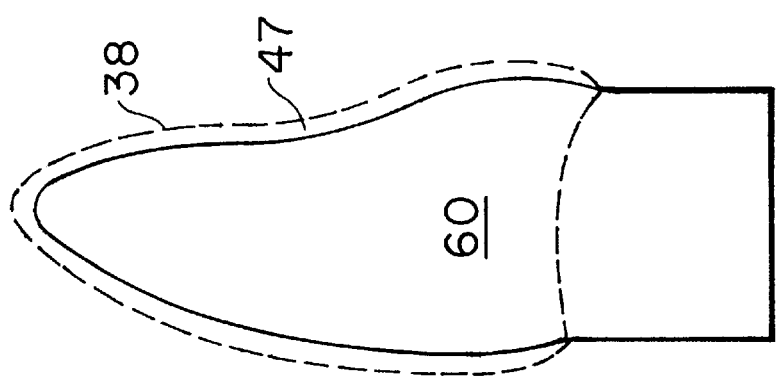
FIG. 13 shows application of a die lubricant or release agent over the die spacer.

In FIG. 13 is shown application of the lubricant or release agent 38 over the die spacer 47.

Following application of the lubricant, a dental wax build-up 62, intended to replicate the geometry of tooth preparation 54, is applied over said lubricant 38 and die spacer 47.

Figure 14:
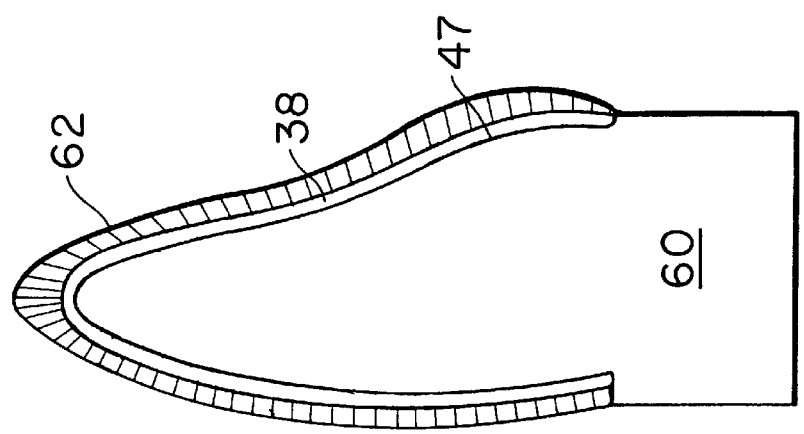
FIG. 14 shows the application of wax build-up having the geometry of the desired substructure.

See FIG. 14.

Figure 15:
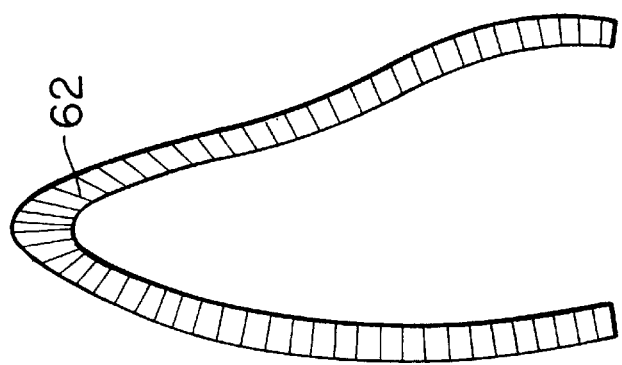
FIG. 15 shows the removal of the wax build-up from the dental die.

Shown in FIG. 15 is removal of the wax-up 62 from the die 60.

Following the step of FIG. 15, the wax-up is subjected to a laboratory process (see FIG. 16), which process may differ from material to material. This process may entail steps such as sprueing, investing, and pressing at high temperatures, of the translucent dental material such as a flowable or pressable ceramic, to thereby achieve a replication of the wax build up 62. Thereby, a translucent dental material substructure 64 is produced and, with it, an approximation of a "full contour" geometry 70 of the ultimate translucent restoration.

Figure 16:
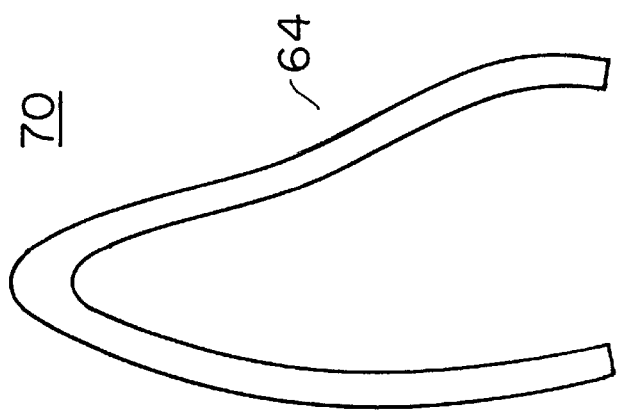
FIG. 16 indicates the result of a laboratory process by which the wax build-up of FIG. 15 is converted to a ceramic or translucent material.

Following the step of FIG. 16 (see FIG. 17), the translucent substructure 64 is placed upon said die 60, over which still remains die spacer 47. However, a wetting agent 66 is preferably placed over spacer 47 before positioning of the substructure 64 thereupon. The wetting agent assures more accurate color between the die spacer 47 and the substructure 64. It is noted that the shade of the die spacer 47 is visible through the substructure 64 and, as such, will influence shading and color determination.

Shown in FIG. 18 is the translucent substructure 64 after any necessary color adjustment have occurred. Such adjustments are shown as layer 68 in FIG. 18 therein.

Shown in FIG. 19 is the addition of a layer of a translucent bonding agent or resin 48 to the interior of the translucent substructure 64. It is of course to be appreciated that, following finalization of the color transmission of the substructure 64, through the use of successive layering, or other means, the geometry of the translucent and shaded dental material 70, such as flowable or pressable ceramic, will be finalized to shape of the original tooth 52 (see FIG. 7) of the patient. After this has bean accomplished, bonding of the translucent substructure 64, using said bonding agent 48 to the tooth stump or preparation 54 is accomplished, as is shown in FIG. 20.

Shown in FIGS. 21 through 23 is a comparison of the optical properties of prior art restorations with that of the present translucent restoration without opacious substructure, i.e., the product of the method of the present invention. As may be noted in FIG. 21, with porcelain fused to metal (PFM) technology, light is entirely blocked by the metal coping 36. As such, a dark background existed in all PFM restorations. Accordingly, considerable color correction was always required to offset the dark background of the metal coping 36. In addition, the opaque layer 40 operated to minimize refraction that might otherwise have occurred. Also, since light could not penetrate the coping or the opaque layer, the resultant restoration, regardless of how well it might be color corrected, would still not appear lifelike.

In FIG. 22 is shown the optics associated with the DICOR system without need for a separate tooth stump of dentin shade. Therein, light can slightly penetrate the color corrected cement 44; however, for the reasons set forth in the Background of the Invention, the use of cement for purposes of color matching cannot produce an optical effect comparable to that of the instant invention. This may be more fully appreciated with reference to FIG. 23 wherein, as may be noted, due to the use of the translucent bonding resin 65, in combination with the novel use of the die spacer 47 (see FIGS. 17 to 20) to match the color and shade prescribed by the dentist, and further in view of the single die method above described, results in a system which provides optical transmission through the restoration and the tooth stump and as well accurate color transmission therebetween. Accordingly, by use of the die spacer as a means of color matching of the restoration to the original tooth and tooth stump, much improved optical and chromatic results are obtained.

Figure 25:
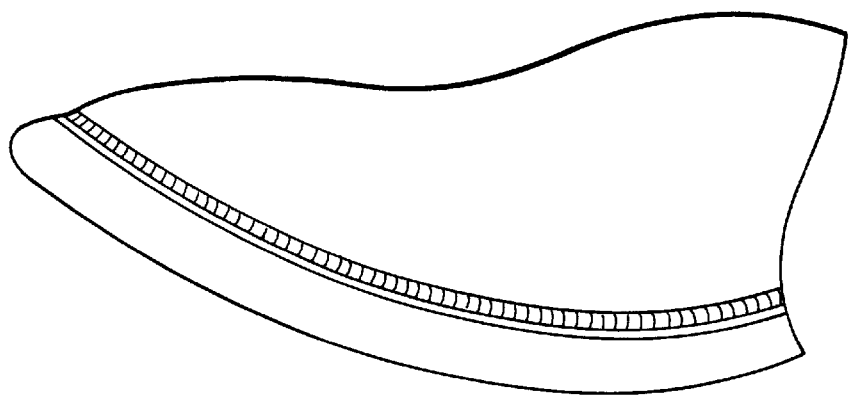
FIG. 25 is a schemative view showing application of the present method to a veneer or laminate enhancement of a tooth.
Figure 24:
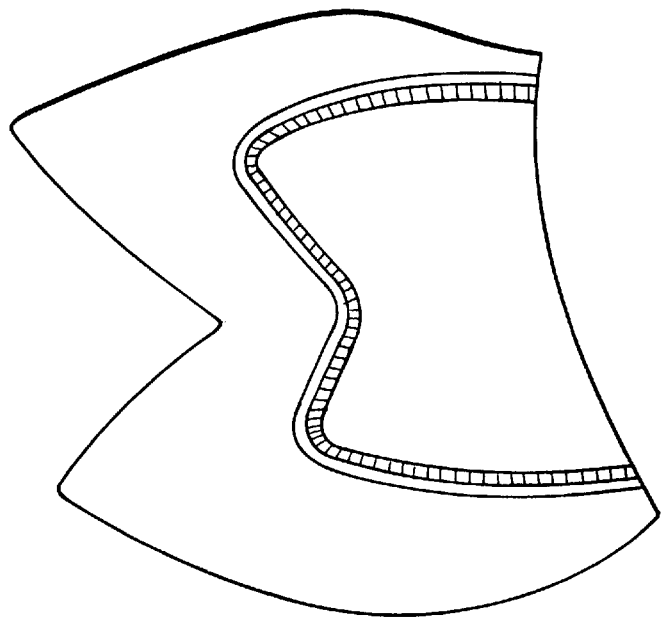
FIG. 24 is a schematic view of a restoration in accordance with the present method used in restoration of a posterior tooth.
Figure 27:
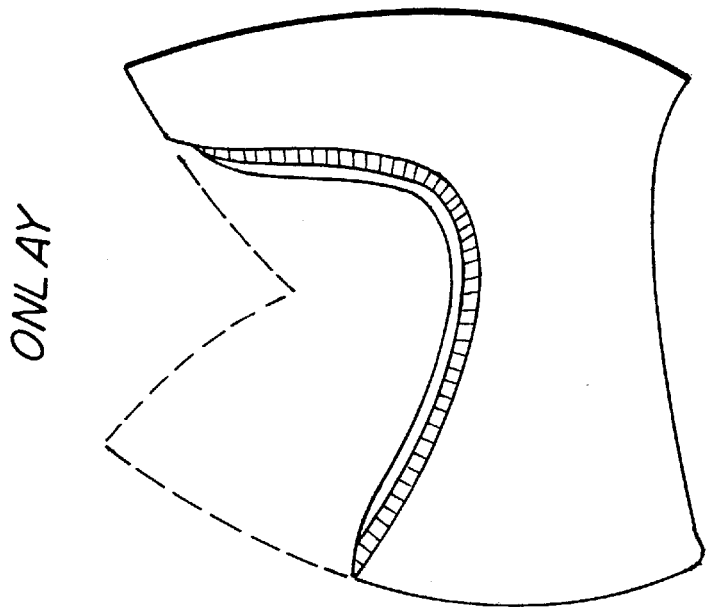
FIG. 27 is a schematic view showing application of the inventive method to a dental onlay.
Figure 26:
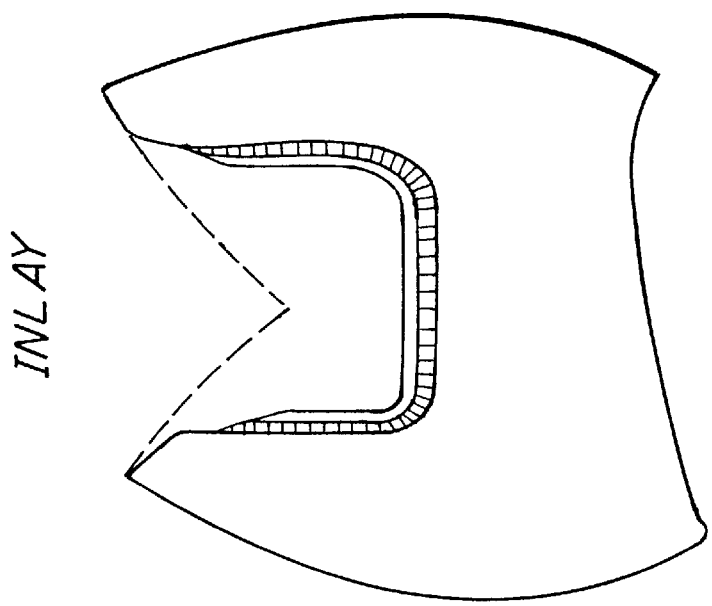
FIG. 26 is a schematic view showing application of a present method to a dental inlay.
Figure 28A:
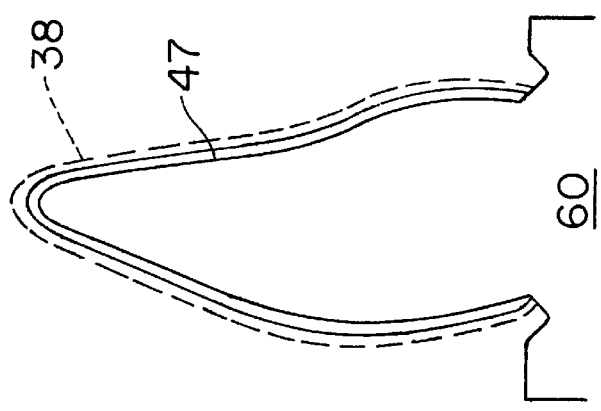
FIGS. 28A–28E are schematic views showing use of the present method with a leucite material.
Figure 28B:
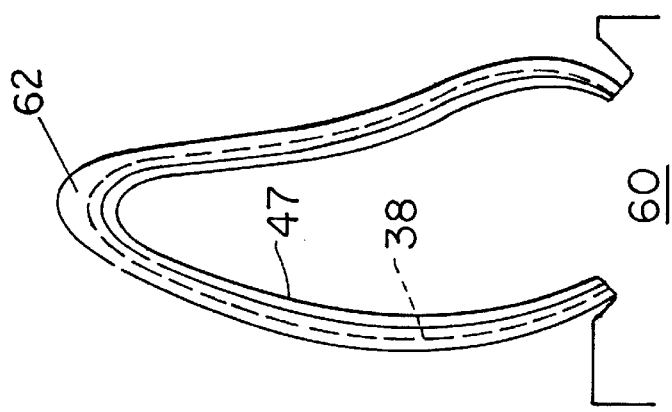
Figure 28C:
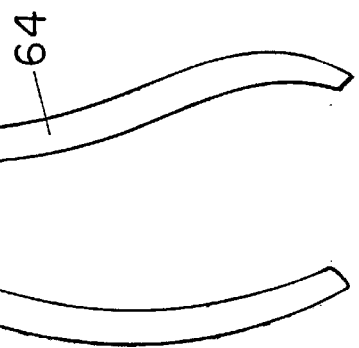
Figure 28E:
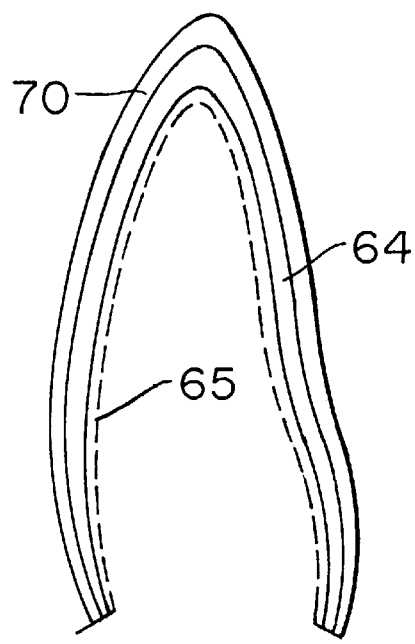
Figure 28D:
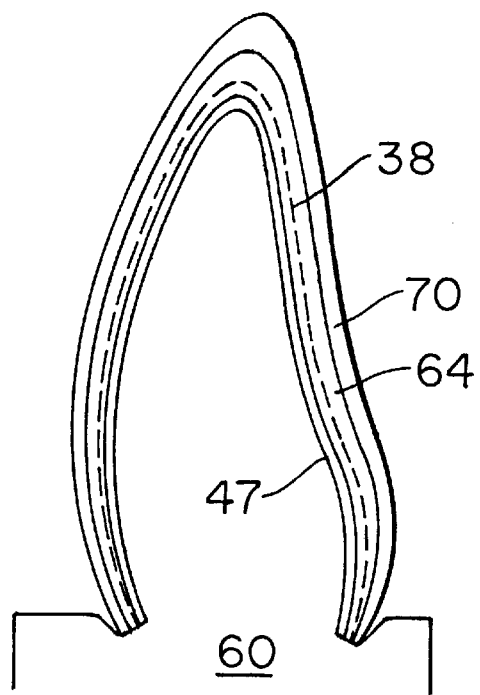
Figure 29C:
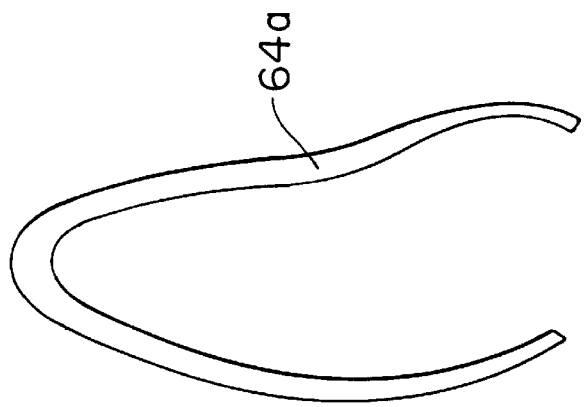
FIGS. 29A–29E are schematic views showing use of the present method with composite polymers or hybrid materials.
Figure 29B:
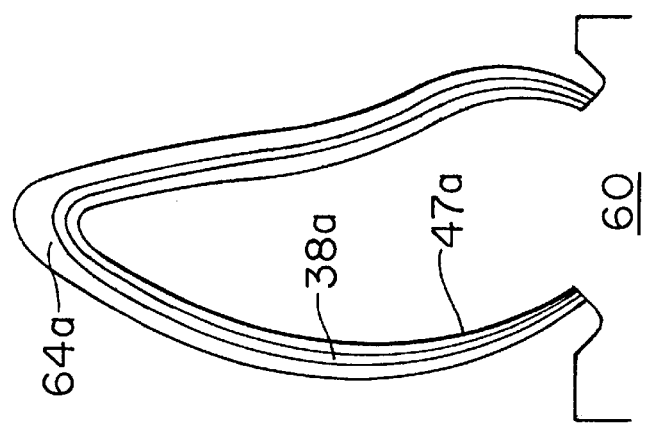
Figure 29A:
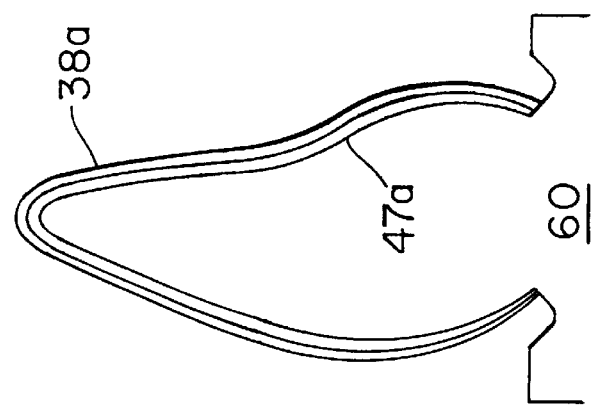
Figure 29E:
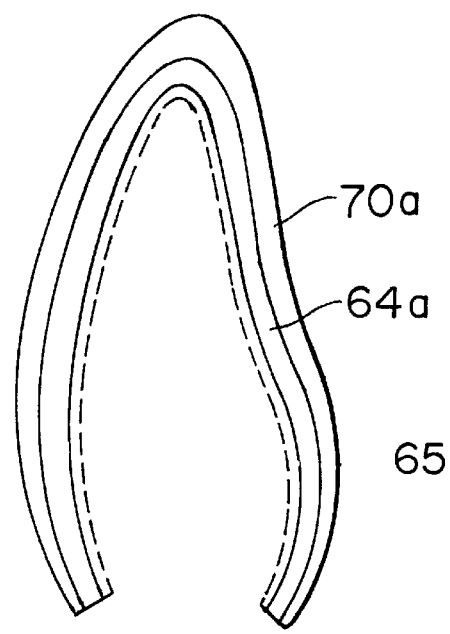
Figure 29D:
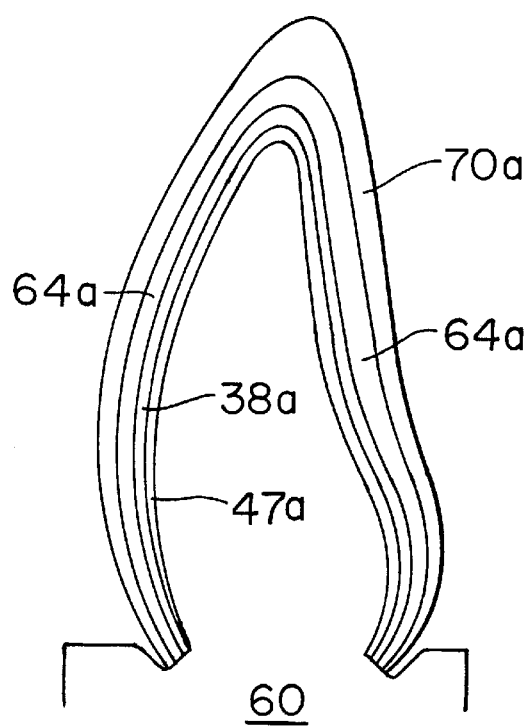

In FIGS. 24 through 27 are shown additional types of restorations, that is, in addition to anterior restorations (shown in the prior figures), the instant method may be employed in other types of restorations. For example, FIG. 24 shows a posterior restoration, FIG. 25, a laminate/veneer restoration,. FIG. 25 a dental inlay and FIG. 27 a dental onlay.

Shown in FIG. 28 is application of the instant method to a leucite reinforced restoration, and shown in FIG. 29 is application of the present method to a composite polymer or other resin restoration.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth.

It is noted that FIG. 28 consists, more particularly, of Sub-figures A through E. Sub-figure A (which generally corresponds to said FIG. 13) shows the tooth die 60 and, thereupon die spacer 47 and die release agent 38. In Sub-figure B (which generally corresponds to said FIG. 14 is shown the addition of dental wax build-up 62. Sub-figure C shows the release of the wax build-up and its formation into translucent substructure 64.

In Sub-figure D is shown the die with the die spacer lubricant or release agent 38 and the translucent porcelain, ceramic or lucite substructure 64. Upon this is placed the correct shading of ceramic material 70, called the extrinsic shading. This also completes the correct shape of the tooth (which may not necessarily be that of the original tooth if the original tooth were broken or deformed). In Sub-figure D the shade of the die spacer represents the dentin shade prescribed by the dentist and therefore used by the technician, this enabling a more correct shade match of the extrinsic shade of the porcelain because both the dentin shade from within and the extrinsic shade from the surface represents the total shade of the porcelain as viewed by the dentist and technician. In Sub-figure E is shown the finished porcelain or pressed ceramic geometry that has both the clear ceramic substructure 64 and the extrinsic or external enamel shade baked over it. This shell has a translucent bonding resin 65 coated over its inner surface to enable bonding to the natural tooth structure.

With reference to the FIG. 29 there is shown an embodiment of the present method for tooth build-up materials including, without limitation, composite, hybrid and other restorative resins and materials not made of a metallic or opacious substructure. More particularly, in Sub-figure A of FIG. 29 is shown a dentin colored die spacer 47a

Having thus described our invention what we claim as new, useful and non-obvious and, accordingly, secure by Letters Patent of the United States is:

1. A method of fabrication of dental translucent restorations without opacious substructures, the method comprising the steps of:
   (a) applying an impression material to a tooth stump;
   (b) using the geometry of an impression resultant of said applying Step (a) to form a dental die;
   (c) applying, upon said die, a die spacer, the color and shade of which is matched to a dentist's prescription of the dentin shade;
   (d) applying a lubricant to said die spacer;
   (e) applying, upon said lubricant, a dental wax from which a dental wax-up is formed;
   (f) removing said wax-up from said die; and
   (g) processing said wax-up into a translucent dental substructure matching said prescribed color and shade.

2. The method as recited in claim 1, further comprising the step of:
   (h) applying a translucent bonding material to an interior surface of said substructure prior to bonding to said tooth stump.

3. The method as recited in claim 2, further comprising the step of:
   (i) internesting said substructure resultant of Step (g) with said die of Step (b) to thereby ascertain the extent of chromatic and geometry conformity therebetween.

4. The method as recited in claim 2, further comprising the step of:
   (j) employing a wetting agent between said substructure and said die to form a more accurate color transmission therebetween.

5. The method as recited in claim 2, in which said dentist's prescription of Step (c) above includes specification of extrinsic and intrinsic tooth coloration.

6. The method as recited in claim 2, further comprising the step of:
   using said substructure as a foundation upon which to build up a restoration having thereon a prescribed enamel color.

* * * * *